(12) United States Patent
Vaysse-Ludot et al.

(10) Patent No.: US 7,214,805 B2
(45) Date of Patent: May 8, 2007

(54) PROCESS FOR THE INDUSTRIAL SYNTHESIS OF STRONTIUM RANELATE AND ITS HYDRATES

(75) Inventors: Lucile Vaysse-Ludot, Saint-Wandrille-Rancon (FR); Jean-Pierre Lecouve, Le Havre (FR); Pascal Langlois, Saint Jean de la Neuville (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 287 days.

(21) Appl. No.: 10/669,301

(22) Filed: Sep. 24, 2003

(65) Prior Publication Data

US 2004/0063972 A1  Apr. 1, 2004

(30) Foreign Application Priority Data

Sep. 24, 2002 (FR) ................... 02 11763

(51) Int. Cl.
*C07D 333/02* (2006.01)
*C07D 265/30* (2006.01)

(52) U.S. Cl. ............................ 549/61; 544/106; 549/29
(58) Field of Classification Search ................ 549/29, 549/61; 544/106
See application file for complete search history.

(56) References Cited

U.S. PATENT DOCUMENTS 5,128,367 A  7/1992 Wierzbicki et al.

7,091,364 B2 *  8/2006  Vaysse-Ludot et al. ....... 549/61
7,105,683 B2 *  9/2006  Vaysse-Ludot et al. ....... 549/61

FOREIGN PATENT DOCUMENTS

| EP | 0 415850 A1 * | 3/1991 |
| EP | 0415850 | 3/1991 |
| EP | 0813869 | 12/1997 |

OTHER PUBLICATIONS

Eurasian Search Report for Eurasian Application No. 200300925, Dec. 18, 2003.
International Search Report for International No. PCT/FR2003/002777, Feb. 5, 2004.
Wierzbicki, et al., Bull. Chim. Soc. Fr., 1975, 7-8, 1786-1792.

* cited by examiner

*Primary Examiner*—Golam M. M. Shameem
(74) *Attorney, Agent, or Firm*—Hueschen and Sage

(57) ABSTRACT

The process for the industrial The synthesis of strontium ranelate of formula (I):

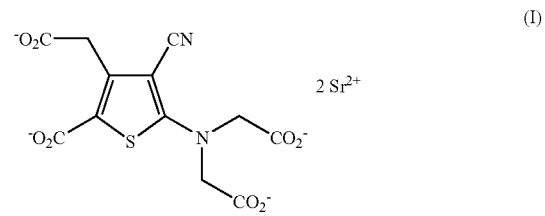

and its hydrates.

17 Claims, No Drawings

PROCESS FOR THE INDUSTRIAL SYNTHESIS OF STRONTIUM RANELATE AND ITS HYDRATES

BACKGROUND OF THE INVENTION

The present invention relates to a process for the industrial synthesis of strontium ranelate of formula (I):

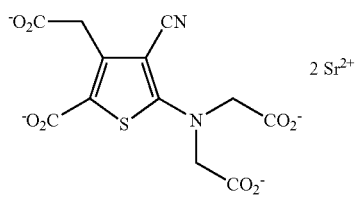

(the distrontium salt of 5-[bis(carboxymethyl)amino]-3-carboxymethyl-4-cyano-2-thiophenecarboxylic acid), and its hydrates.

Strontium ranelate has very valuable pharmacological and therapeutic properties, especially pronounced anti-osteoporotic properties, making this compound useful in the treatment of bone diseases.

Strontium ranelate, its preparation and its therapeutic use have been described in the European Patent Specification EP 0 415 850.

However, industrial production of a compound such as strontium ranelate requires detailed study of all the reaction steps and of the selection of starting materials, reagents and solvents in order to obtain optimum yields.

The Applicant has developed a synthesis process for strontium ranelate of formula (I) in which such conditions have been combined, resulting in the use of a whole group of especially valuable methods and procedures.

DESCRIPTION OF THE PRIOR ART

The Patent Specification EP 0 415 850 describes the synthesis of strontium ranelate starting from the ethyl tetraester of formula (IIa):

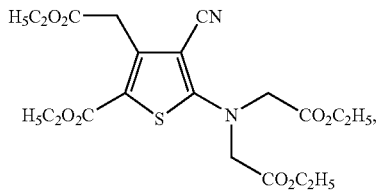

which is itself obtainable starting from the ethyl diester of formula (IIIa):

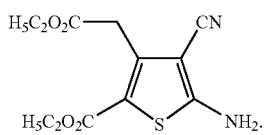

Synthesis of the intermediate of formula (IIIa) has been described in the publication Bull. Soc. Chim. France 1975, pp. 1786–1792 and in the publication J. Chem. Tech. Biotechnol. 1990, 47, pp. 39–46, by reaction between diethyl 3-oxoglutarate, malononitrile and sulphur in ethanol, in the presence of morpholine or diethylamine.

That process has the advantage of using readily accessible starting materials and of being simple to put into practice; however, when transferred to the scale of several hundred kilograms, it does not allow the compound of formula (IIIa) to be obtained in a yield greater than 70%.

DETAILED DESCRIPTION OF THE INVENTION

In order to synthesise strontium ranelate of formula (I) industrially, the Applicant has developed an effective industrial synthesis process allowing the intermediate of formula (III):

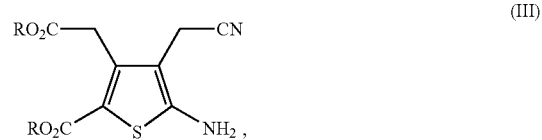

wherein R represents a linear or branched ($C_1$–$C_6$)alkyl group, to be obtained with a purity greater than 97% and in a yield of 77%, which is reproducible on an industrial scale.

More specifically, the industrial synthesis of the diester of formula (III) which has been developed by the Applicant for the industrial synthesis of strontium ranelate of formula (I) uses, as starting material, the compound of formula (IV):

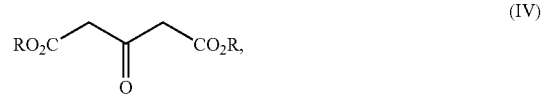

wherein R is as defined hereinbefore,
which is reacted with malononitrile of formula (V):

in methanol,
in the presence of morpholine in an amount greater than 0.95 mol per mol of compound of formula (IV),
to yield the compound of formula (VI):

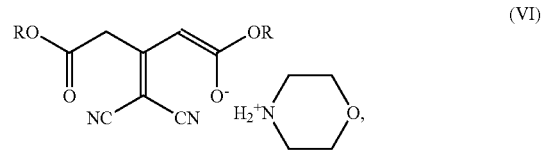

wherein R is as defined hereinbefore,
which is then reacted with sulphur in an amount greater than 0.95 mol per mol of compound of formula (IV);
the reaction mixture is then heated at reflux;
and the compound of formula (III) thereby obtained is isolated by precipitation in the presence of water, followed by filtration.

The process, accordingly improved by the use of these very specific conditions, and especially by the intermediate formation of the compound of formula (VI), which can, if desired, be isolated, allows the compound of formula (III) to be obtained with excellent purity and in a yield of at least 77% which is reproducible on the scale of several hundred kilograms, which represents a major gain in yield in view of the large tonnages of strontium ranelate produced.

The amount of methanol is preferably from 1 to 3 ml per gram of compound of formula (IV).

The temperature of reaction between the compounds of formulae (IV) and (V) is preferably less than 50° C.

The reaction time at reflux after addition of the sulphur is preferably from 1 hour 30 minutes to 3 hours.

The second step in the process for the industrial synthesis of strontium ranelate of formula (I) developed by the Applicant comprises converting the compound of formula (III) into the compound of formula (II):

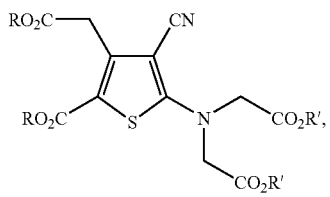

wherein R is as defined hereinbefore and R' represents a linear or branched $(C_1–C_6)$alkyl group.

The journal Bull. Soc. Chim. France 1975, pp. 1786–1792, describes obtaining the compound of formula (IIa), a particular case of the compounds of formula (II) wherein R=R'=ethyl), by reacting 5-amino-3-(carboxymethyl)-4-cyano-2-thiophenecarboxylic acid with ethyl bromoacetate, in the presence of potassium carbonate, followed by isolation in a highly dilute aqueous-organic medium.

However, the low yield of that reaction (65%), the large amount of aqueous saline waste generated by that reaction and, above all, the very long reaction time (5 days) have completely precluded the use of that reaction on an industrial scale.

In order to synthesise strontium ranelate of formula (I) industrially, the Applicant has developed a simple industrial synthesis process which allows the compound of formula (II) to be obtained in a very good yield, with a considerably shorter reaction time and excellent purity and in which the aqueous saline waste is completely avoided.

More specifically, the industrial synthesis of the tetraester of formula (II) which has been developed by the Applicant for the synthesis of strontium ranelate of formula (I) uses, as starting material, the compound of formula (III):

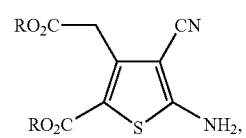

wherein R represents a linear or branched $(C_1–C_6)$alkyl group,
which is reacted with a compound of formula (VII):

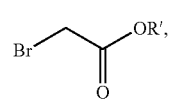

wherein R' represents a linear or branched $(C_1–C_6)$alkyl group,
in the presence of a catalytic amount of a $C_8–C_{10}$-type quaternary ammonium compound,
and in the presence of potassium carbonate,
at the reflux of an organic solvent;
the reaction mixture is subsequently filtered;
the mixture is then concentrated by distillation;
a co-solvent is then added,
and the reaction mixture is cooled and filtered
to yield, after drying of the powder thereby obtained, the compound of formula (II).

A $C_8–C_{10}$-type quaternary ammonium compound is understood to be a compound of formula (A) or a mixture of compounds of formula (A):

wherein $R_1$ represents a $(C_1–C_6)$alkyl group, $R_2$, $R_3$ and $R_4$, which are the same or different, each represent a $(C_8–C_{10})$alkyl group, and X represents a halogen atom.

$C_8–C_{10}$-type quaternary ammonium compounds to which preference is given are the catalysts Adogen 464® and Aliquat 336®.

Surprisingly, only the use of a $C_8–C_{10}$-type quaternary ammonium compound allows the compound of formula (I) to be obtained both with a greatly reduced reaction time and with very good selectivity, in contrast to other types of quaternary ammonium compounds, as the following Table shows:

| Catalyst | Duration of reaction | Content of reaction mixture |
|---|---|---|
| Tetrabutylammonium hydrogen sulphate (TBAHS) | 12 hours | 92% |
| N,N-bis(2-hydroxyethyl)-N-methyl 1-dodecanaminium bromide | 18 hours | 82% |
| Adogen 464 ® | 5 hours | 96% |
| Aliquat 336 ® | 4 hours | 95% |

Furthermore, the somewhat simplified isolation (the precipitation step followed by filtration has been replaced by simple filtration of the reaction mixture) allows, by virtue of the particular conditions developed, the compound of formula (II) to be obtained not only in a very good yield (89%) but also with excellent purity (greater than 98%), whilst avoiding the burden on the environment that the aqueous saline waste represented.

The amount of potassium carbonate is preferably from 2 to 3 mol per mol of compound of formula (III).

The amount of compound of formula (VII) is preferably from 2 to 3 mol per mol of compound of formula (III).

The initial volume of organic solvent is preferably from 6 to 12 ml per gram of compound of formula (III).

The organic solvents that are preferred for the reaction are acetone and acetonitrile.

The co-solvent that is preferred for isolation is methanol.

The third and final step in the process for the industrial synthesis of strontium ranelate of formula (I) developed by the Applicant comprises converting the tetraester of formula (II) into the distrontium salt of the corresponding tetraacid.

The Patent Specification EP 0 415 850 describes three methods for that conversion. The third of the methods described, which comprises heating the compound of formula (IIa), a particular case of the compounds of formula (II), in an aqueous alcoholic medium, with strontium hydroxide, and then distilling off the ethanol and isolating the compound of formula (I) by precipitation, has the advantage of being extremely simple to perform.

However, whilst operating under the conditions described for that third method, the Applicant has obtained strontium ranelate only in a yield of 80% and with a purity of 87%.

In view of the fact that strontium ranelate is insoluble in most solvents, its subsequent purification is extremely laborious. Such a method has therefore been incompatible with use of the strontium ranelate as a pharmaceutical active ingredient, which requires a purity greater than or equal to 98%.

The Applicant has developed an industrial synthesis process allowing strontium ranelate to be obtained not only with excellent chemical purity so that it does not require further treatment before being used as a pharmaceutical active ingredient but also in an excellent yield.

More specifically, the final step in the process for the industrial synthesis of strontium ranelate of formula (I) developed by the Applicant uses the compound of formula (I):

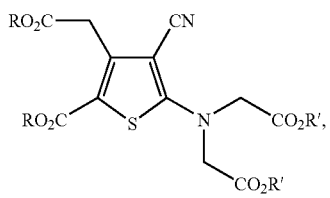

(II)

wherein R and R', which are the same or different, each represent a linear or branched $(C_1-C_6)$alkyl group, R preferably representing a methyl group and R' preferably representing a methyl or ethyl group, which is reacted with strontium hydroxide in an amount greater than or equal to 2 mol per mol of compound of formula (II),
at the reflux of water,
for at least 5 hours;
the precipitate obtained is then filtered off whilst hot;
the cake obtained is washed with boiling water
to yield, after drying of the powder thereby obtained, the compound of formula (I) and its hydrates.

Surprisingly, replacement of the ethanol/water mixture by water alone dramatically improves not only the purity of the strontium ranelate obtained but also the yield.

Moreover, dispensing with the ethanol distillation step further simplifies the process.

The amount of water in the reaction mixture is preferably greater than or equal to 8 ml per gram of compound of formula (II).

The amount of strontium hydroxide is preferably from 2 to 2.5 mol per mol of compound of formula (II).

The Examples hereinbelow illustrate the invention but do not limit it in any way.

Examples 1A and 1B illustrate the first step in the Applicant's process for the industrial synthesis of strontium ranelate; Examples 2A, 2B, 2C and 2D illustrate the second step in that process; finally, Example 3 illustrates the third and last step in that process.

EXAMPLE 1A

Methyl 5-amino-4-cyano-3-(2-methoxy-2-oxoethyl)-2-thiophene-carboxylate

Introduce into a reactor 400 kg of dimethyl 3-oxoglutarate, 158 kg of malononitrile and 560 liters of methanol and then, whilst maintaining the temperature of the reaction mixture below 40° C., 199.6 kg of morpholine.

Then introduce 73.6 kg of sulphur and subsequently bring the mixture to reflux.

After reacting for 2 hours, stop refluxing and add water until precipitation occurs. Filter off the precipitate obtained, wash it and dry it.

Methyl 5-amino-4-cyano-3-(2-methoxy-2-oxoethyl)-2-thiophenecarboxylate is thereby obtained in a yield of 77% and with a chemical purity of 98%.

EXAMPLE 1B

Methyl 5-amino-4-cyano-3-(2-methoxy-2-oxoethyl)-2-thiophene-carboxylate

Introduce into a reactor 400 kg of dimethyl 3-oxoglutarate, 158 kg of malononitrile and 560 liters of methanol and then, whilst maintaining the temperature of the reaction mixture below 40° C., 199.6 kg of morpholine.

The compound of formula (VI) thereby obtained, or the addition salt of methyl 3-(dicyanomethylene)-5-hydroxy-5-methoxy-4-pentenoate with morpholine, is isolated by filtration after cooling of the mixture and is then reacted with 73.6 kg of sulphur in methanol.

The mixture is then brought to reflux.

After reacting for 2 hours, stop refluxing and add water until precipitation occurs. Filter off the precipitate obtained, wash it and dry it.

EXAMPLE 2A

Methyl 5-[bis(2-methoxy-2-oxoethyl)amino]-4-cyano-3-(2-methoxy-2-oxoethyl)-2-thiophenecarboxylate Introduce into a reactor 400 kg of 5-amino-3-(carboxymethyl)-4-cyano-2-thiophene-carboxylic acid, 478 kg of potassium carbonate, 2810 liters of acetone, 16 kg of Adogen 464® and 529.6 kg of methyl bromoacetate.

Bring the temperature to 60° C. After refluxing for 5 hours, cool the reaction mixture and then filter it. Concentrate the filtrate obtained.

Add methanol; cool and filter the suspension obtained, and then dry the powder.

Methyl 5-[bis(2-methoxy-2-oxoethyl)amino]-4-cyano-3-(2-methoxy-2-oxoethyl)-2-thiophenecarboxylate is thereby obtained in a yield greater than 85% and with a chemical purity greater than 98%.

EXAMPLE 2B

Methyl 5-[bis(2-methoxy-2-oxoethyl)amino]-4-cyano-3-(2-methoxy-2-oxoethyl)-2-thiophenecarboxylate Methyl 5-[bis(2-methoxy-2-oxoethyl)amino]-4-cyano-3-(2-methoxy-2-oxoethyl)-2-thiophenecarboxylate is obtained in the same manner as Example 1, but replacing Adogen 464® by Aliquat 336®.

EXAMPLE 2C

Methyl 5-[bis(2-methoxy-2-oxoethyl)amino]-4-cyano-3-(2-methoxy-2-oxoethyl)-2-thiophenecarboxylate Methyl 5-[bis(2-methoxy-2-oxoethyl)amino]-4-cyano-3-(2-methoxy-2-oxoethyl)-2-thiophenecarboxylate is obtained in the same manner as Example 1, but replacing the acetone by acetonitrile.

EXAMPLE 2D

Methyl 5-[bis(2-ethoxy-2-oxoethyl)amino]-4-cyano-3-(2-methoxy-2-oxoethyl)-2-thiophenecarboxylate Methyl 5-[bis(2-ethoxy-2-oxoethyl)amino]-4-cyano-3-(2-methoxy-2-oxoethyl)-2-thiophenecarboxylate is obtained in the same manner as Example 1, but replacing the 529.6 kg of methyl bromoacetate by 578.1 kg of ethyl bromoacetate.

EXAMPLE 3

5-[Bis(carboxymethyl)amino]-3-carboxymethyl-4-cyano-2-thiophenecarboxylic acid distrontium salt octahydrate Introduce into a reactor 770 kg of strontium hydroxide and 5,500 liters of water and then 550 kg of methyl 5-[bis(2-methoxy-2-oxoethyl)amino]-4-cyano-3-(2-methoxy-2-oxo-ethyl)-2-thiophenecarboxylate. Heat to reflux and continue refluxing for a minimum of 5 hours; then filter the reaction mixture whilst hot, wash the cake with boiling water and dry the powder obtained.

5-[Bis(carboxymethyl)amino]-3-carboxymethyl-4-cyano-2-thiophenecarboxylic acid distrontium salt octahydrate is thereby obtained in a yield of 96% and with a chemical purity of 98%.

We claim:

1. A process for the industrial synthesis of strontium ranelate of formula (I):

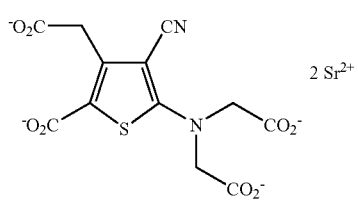

(I)

and its hydrates,
wherein a compound of formula (II):

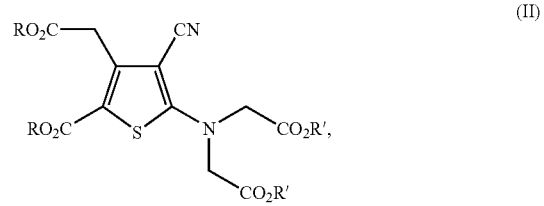

(II)

wherein R and R', which may be identical or different, each represent linear or branched ($C_1$—$C_6$)alkyl,
is reacted with strontium hydroxide in an amount greater than or equal to 2 mol per mol or compound of formula (II),
at reflux with water,
for at least 5 hours;
the precipitate obtained is then filtered off while hot;
the cake obtained is washed with boiling water
to yield, after drying of the powder thereby obtained, the compound of formula (I) and its hydrates.

2. The synthesis process of claim 1, wherein the amount of water used in the reaction of the compound formula (II) with strontium hydroxide is greater an or equal to 8 ml per gram of compound of formula (II).

3. The synthesis process of claim 1, wherein the amount of strontium hydroxide is from 2 to 2.5 mol per mol of compound of formula (II).

4. The synthesis process of claim 1, wherein R represents methyl and R' represents methyl or ethyl.

5. A process for the industrial synthesis of strontium ranelate of formula (I):

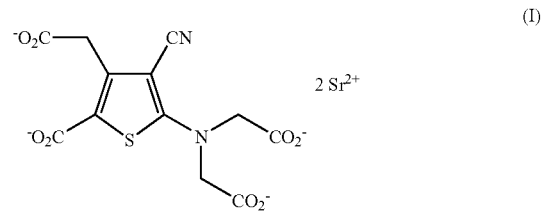

(I)

and its hydrates,
wherein a compound of formula (IV):

(IV)

wherein R represents linear or branched ($C_1$—$C_6$)alkyl,
is reacted with malononitrile of formula (V):

(V)

in methanol,
in the presence of morpholine in an amount greater than 0.95 mol per mol of compound of formula (IV), to yield the compound of formula (VI):

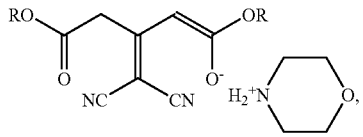

which is then reacted with sulphur in an amount greater than 0.95 mol per mol of compound of formula (IV);

the reaction mixture is then heated at reflux;

and the compound thereby obtained is isolated by precipitation in the presence of water, followed by filtration, to yield the compound of formula (III):

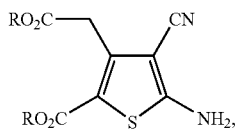

which is reacted with a compound of formula (VII):

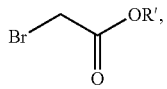

wherein R' represents linear or branched $(C_1-C_6)$alkyl, in the presence of a catalytic amount of a $c_8-C_{10}$—type quaternary ammonium compound, and in the presence of potassium carbonate, at reflux with an organic solvent;

the reaction mixture is subsequently filtered;

the mixture is then concentrated by distillation;

a co-solvent is then added, and the reaction mixture is cooled and filtered to yield, after drying of the powder thereby obtained, the compound of formula (II):

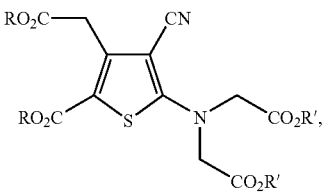

which is reacted with strontium hydroxide according to the process of claim 1.

6. The synthesis process of claim 5, wherein the amount of methanol used in the synthesis of the compound of formula (III) is from 1 to 3 ml per gram of compound of formula (IV).

7. The synthesis process of claim 5, wherein the temperature of reaction between the compounds of formulae (IV) and (V) is less than 50° C.

8. The synthesis process of claim 5, wherein the refluxing time for the reaction between the compound of formula (VI) and sulphur is between 1 hour 30 minutes and 3 hours.

9. The synthesis process of claim 5, wherein the amount of potassium carbonate used in the synthesis of the compound of formula (II) is from 2 to 3 mol per mol of compound of formula (III).

10. The synthesis process of claim 5, wherein the amount of compound of formula (VII) is from 2 to 3 mol per mol of compound of formula (III).

11. The synthesis process of claim 5, wherein the initial volume of organic solvent used in the reaction of the compound of formula (III) with the compound of formula (VII) is from 6 to 12 ml per gram of compound of formula (III).

12. The synthesis process of claim 5, wherein the organic solvent used in the reaction of the compound of formula (III) with the compound of formula (VII) is acetone or acetonitrile.

13. The synthesis process of claim 5, wherein the co-solvent used in the isolation of the compound of formula (II) is methanol.

14. The synthesis process of claim 5, wherein the compound of formula (II) obtained has a chemical purity greater than 98 %.

15. The synthesis process of claim 5, wherein the amount of water used in the reaction of the compound of formula (II) with strontium hydroxide is greater than or equal to 8 ml per gram of compound of formula (II).

16. The synthesis process of claim 5, wherein the amount of strontium hydroxide is from 2 to 2.5 mol per mol of compound of formula (II).

17. The synthesis process of claim 5, wherein R represents methyl and R' represents methyl or ethyl.

* * * * *

UNITED STATES PATENT AND TRADEMARK OFFICE
CERTIFICATE OF CORRECTION

PATENT NO. : 7,214,805 B2  Page 1 of 1
APPLICATION NO. : 10/669301
DATED : May 8, 2007
INVENTOR(S) : Lucile Vaysse-Ludot et al.

It is certified that error appears in the above-identified patent and that said Letters Patent is hereby corrected as shown below:

Column 6, Line 61: "400 kg of" should be --400 kg of the dimethyl ester of--.

Column 7, Line 14: "Example 1" should be --Example 2A--.

Column 7, Line 24: "Example 1" should be --Example 2A--.

Column 7, Line 34: "Example 1" should be --Example 2A--.

Column 8, Line 17: "or" should be --of--.

Column 9, Line 42: "$c_8$-$C_{10}$-" should be -- $C_8$-$C_{10}$- --.

Signed and Sealed this

Eleventh Day of September, 2007

JON W. DUDAS
*Director of the United States Patent and Trademark Office*